United States Patent [19]
Sachinvala

[11] Patent Number: 5,122,601
[45] Date of Patent: Jun. 16, 1992

[54] SYNTHESIS OF 2,3,3',4,4'-PENTA-O-METHYLSUCROSE

[75] Inventor: Navzer D. Sachinvala, Aiea, Hi.

[73] Assignee: Hawaiian Sugar Planters' Association, Aiea, Hi.

[21] Appl. No.: 624,085

[22] Filed: Dec. 7, 1990

[51] Int. Cl.$^5$ .................... C07H 1/00; C07H 5/02; C07H 15/24; C07H 3/04
[52] U.S. Cl. .................... 536/125; 536/120; 536/18.5; 536/13.8; 536/124
[58] Field of Search ........... 536/120, 124, 125, 18.5, 536/13.8; 514/53

[56] References Cited

U.S. PATENT DOCUMENTS

| | | | |
|---|---|---|---|
| 3,042,666 | 7/1962 | Gentles | 536/120 |
| 4,493,831 | 1/1985 | Takaya et al. | 536/13.8 |
| 4,783,526 | 11/1988 | O'Brien et al. | 536/18.5 |
| 4,801,700 | 1/1989 | Tully et al. | 536/125 |
| 4,920,207 | 4/1990 | Sankey et al. | 536/125 |

OTHER PUBLICATIONS

Moody et al., "Isolation and alkaline degradation of some mono-O-methylsucroses", Carbohyd. Res., vol. 114 (1983), pp. 306–310.

O'Donnell et al., "Synthesis of Some Partially Methylated Sucrose Derivatives", Aust. J. Chem., vol. 25 (1972), pp. 407–412.

Ogata et al., "Molecular Weight Control in Polycondensation of Hydroxyl Diesters with Hexamethylenediamine by Polymer Matrices", Journal of Polymer Science: Polymer Chemistry Edition, vol. 19 (1981), pp. 2609–2617.

Dirlikov, "Monomers and Polymers based on Mono- and Dissaccharides", Pacific Polymer Preprints, vol. 1 (Nov. 1989), pp. 113–114.

Hough et al., "Sucrochemistry. Part II. 6,6'-Di-O-tritylsucrose", Carbohyd. Res., vol. 21 (1972), pp. 144–147.

McKeown et al., "Selective Substitution in Sucrose. II. The Synthesis of 2,3,3',4,4'-Penta-O-Methyl Sucrose and $C_4$ to $C_6$ Acetyl Migration in Sucrose", Canadian Journal of Chemistry, vol. 35 (1987), pp. 992–997.

Dirlikov, "Monomes and Polymers based on Mono-and Disaccharides", Pacific Polymer Prepints, vol. 1, (Dec. 12–15, 1989), pp. 113–114.

Primary Examiner—Ronald W. Griffin
Assistant Examiner—Louise Leary
Attorney, Agent, or Firm—Burns, Doane, Swecker & Mathis

[57] ABSTRACT

A process for manipulating any polyhydroxy compound bearing two or more primary and secondary hydroxyl groups to expose only the primary hydroxyl groups, while blocking all interfering secondary hydroxyl groups as their methyl or other alkyl ethers. More particularly, the present invention relates to the synthesis of 2,3,3',4,4'-penta-O-methylsucrose by using this method.

20 Claims, 8 Drawing Sheets

SYNTHESIS OF 2,3,3',4,4'-PENTA-O-METHYLSUCROSE

GRANT REFERENCE

The invention described herein was partially funded by U.S.D.A. (A.R.S.) grant number 58-91H2-319.

BACKGROUND OF THE INVENTION

1. Field of the Invention

The present invention relates to a process for manipulating any polyhydroxy compound bearing two or more primary and secondary hydroxyl groups to expose only the primary hydroxyl groups, while blocking all interfering secondary hydroxyl groups as their methyl or other alkyl ethers. More particularly, the present invention relates to the synthesis of 2,3,3',4,4'-penta-O-methylsucrose by using the aforedescribed method.

2. Description of the Prior Art

In the past, many attempts have been made to employ carbohydrates for the development of well-characterized novel polymers of some practical significance. The use of sugars and their derivatives in the production of polymers is of growing interest since polymers containing mono- or disaccharides in their main chain or as grafted pendant groups or chains display useful and unique properties such as hydrophilicity, chirality, biological activity, biodegradability, and the like. Furthermore, most sugars are available at economical prices and are industrially produced in large quantities by cultivation in plants and microorganisms, followed by chemical isolation or by degradation of plant waste material followed by isolation. For instance, sucrose is produced on a scale that is larger than any other pure organic chemical, world-wide.

The major problem associated with the use of carbohydrates for developing polymers is the similar reactivity of the primary and secondary hydroxyl groups on the carbohydrate moiety. Hence, when carbohydrates are polymerized non-enzymatically with other monomers, the resulting polymer products are often a mixture of linear, cross-linked and branched chain products. This is due to the reaction of both the primary and secondary hydroxyl groups in the carbohydrate moiety with electrophilic groups in the other monomer.

Many attempts have been made in the past towards polymerizing carbohydrates such as those attempts described by N. Ogata et al in *J. Polym. Sci.*, Polym. Chem. Ed., Vol. 19, p. 2609 (1981) and Vol. 22, p. 739 (1984); and S. K. Dirlikov, "Monomers and Polymers Based on Mono and Disaccharides", Pacific Polymer Preprints, First Pacific Conference, Dec. 12-15, 1989, Volume 1, pp. 113-114.

Although Dirlikov, supra, claims that high molecular weight polymers have been made, no proof has been shown that these polymers are strictly linear and do not contain additional cross-linked or branched chain polymers and that only the primary hydroxyl groups react thereby forming a strictly linear polymer.

Sucrose used as a starting carbohydrate for the production of carbohydrate polymers would be ideal since it is produced in vast quantities and is low in price. To synthesize intermediate sucrose derivatives for further use in the production of novel polymers using sucrose as a starting compound is difficult due to the reactivity of the primary hydroxyl groups at carbons 6, 1' and 6' and the remaining five secondary hydroxyl groups.

One such sucrose intermediate is 2,3,3',4,4'-penta-O-methylsucrose having the structure:

(I)

The compound of structure (I) is useful as an intermediate in the synthesis of other sucrose derivatives that can be used to synthesize various polymers. This compound has been ambiguously reported by McKeown et al in the *Canadian Journal of Chemistry*, Vol. 35 (1957), p. 992, and subsequently prepared in moderate yields by O'Donnell and Richards as described in the *Australian Journal of Chemistry*, Vol. 25 (1972), pp. 407-412.

However, heretofore, 2,3,3',4,4'-penta-0-methylsucrose has been synthesized by O'Donnell and Richards through several intermediate compounds such as 1',6,6'-tri-O-tritylsucrose, 1',6,6'-tri-O-trityl-2,3,3',4,4'-penta-O-acetylsucrose, and 1',6,6'-tri-O-trityl-2,3,3',4,4'-penta-O-methylsucrose. The final product of 2,3,3',4,4'-penta-0methylsucrose was isolated in the final step by chromatography through amberlite resins, which tend to epimerize the C-1 of the glucopyranoside due to the acidity of these resins. Moreover, the total yield for the synthesis of 2,3,3',4,4'-penta-0-methylsucrose is about 26%, while the yield in the final step is about 79% by using the method described by O'Donnell and Richards.

It has now surprisingly been discovered that 2,3,3',4,4'-penta-O-methylsucrose can be synthesized by eliminating the intermediate compound of 1',6,6'-tri-O-trityl-2,3,4',4,4'-penta-O-acetylsucrose. Moreover, by replacing the amberlite resins with silica gel, the synthesized product does not epimerize at the C-1 position. A marked increase in yield of penta-0-methylsucrose (e.g., yields of up to 97%) is also produced by the present process, thus leading to an intermediate that can be readily produced for use in polymer synthesis.

OBJECTS AND SUMMARY OF THE INVENTION

It is an object of the present invention to avoid or alleviate the problems of the prior art.

It is another object of the present invention to provide a process for manipulating any polyhydroxy compound bearing two or more primary and secondary hydroxyl groups to expose only the primary hydroxyl groups while blocking all interfering secondary hydroxyl groups as their methyl or alkyl ethers, benzyl ethers and allyl ethers.

It is yet another object of the present invention to provide a facile and an improved process for the synthesis of 2,3,3',4,4'-penta-O-methylsucrose, which process produces a marked increase in the overall yield of the final product.

The present invention features a process for the synthesis of a polyhydroxy compound having two or more primary and secondary hydroxyl groups, said process comprising the steps of:

(a) tritylating a polyhydroxy compound having the structure (II):

wherein n is an integer of 1 to 12, to form tri-O-trityl groups on the primary hydroxyl groups;

(b) converting the secondary hydroxyl groups to alkoxides by adding a hydride base to said tritylated compound formed in (a);

(c) alkylating said secondary alkoxides with an alkylating agent; and (d) reducing said primary-O-tritylated groups to form a compound having the structure (III):

wherein n is an integer of from 1 to 12 and R represents a benzyl, allyl, methyl, ethyl, butyl, octyl or alkyl group.

In a preferred aspect, the present invention provides a process for the synthesis of 2,3,3',4,4'-penta-O-methylsucrose comprising the steps of:

(a) converting sucrose to 1',6,6'-tri-O-tritylsucrose with trityl chloride;

(b) treating the converted 1',6,6'-tri-O-tritylsucrose with a hydride base to produce pentasodio 1',6,6'-tri-O-trityl-2,3,3',4,4'-pentaoxysucrate;

(c) alkylating said pentasodio 1',6,6'-tri-O-trityl-2,3,3',4,4'-pentaoxysucrate to form 1',6,6'-tri-O-trityl-2,3,3',4,4'-penta-O-methylsucrose;

(d) reducing the trityl groups with alkali metals in the presence of ammonia to convert the 1',6,6'-tri-O-trityl-2,3,3',4,4'-penta-O-methylsucrose to 2,3,3',4,4'-penta-O-methylsucrose; and (e) isolating 2,3,3',4,4'-penta-O-methylsucrose.

DETAILED DESCRIPTION OF THE PREFERRED EMBODIMENTS OF THE INVENTION

More particularly, the present invention relates to the synthesis of any polyhydroxy compound having two or more primary and secondary hydroxyl groups, wherein the primary hydroxyl groups are maintained and the secondary hydroxyl groups are blocked as their alkyl ethers or methyl ethers. Thus, compounds having the general structure (II):

can be converted to diols having the respective structure (III):

where n in structures (II) and (III) is an integer from 1 to 12, and R in structure (III) represents a benzyl group, allyl group, methyl group, ethyl group, butyl group, octyl group or alkyl group.

Furthermore, any compound bearing primary hydroxyl group appendages and secondary hydroxyl groups on a cyclic hydrocarbon, furan, and/or pyran can also be manipulated as set forth above, as well as other disaccharides such as cellobiose, lactose, gentiobiose, and the like.

Basically, the procedure involves adding to the polyhydroxy compound, a solution of tritylchloride in dimethylformamide over a period of about one hour at a temperature between C to 5° C. The primary hydroxyl groups are tritylated by addition of an excess amount of tritylchloride. The excess amount of tritylchloride used is generally about 4.5 times the molar amount of sucrose.

Then a solution of the trityl adduct is added dropwise to a suspension of a hydride base over a period of about 20 minutes to three hours to convert the secondary hydroxyl groups to alkoxides. Examples of hydride bases that can be used in this process include all group (I) and group (II) metal hydrides. More specifically, sodium hydride, potassium hydride and the like. It is most preferable to use sodium hydride in the present process.

Alternatively, lithium bases can also be used. In the case of alkyl lithium bases, a solution of the lithium base is added to a solution of the polyhydroxy compound at low temperatures. Specific examples of lithium bases include methyllithium, butyllithium, t-butyllithium, phenyllithium and the like.

The amount of hydride used in the reaction may vary depending on the amount of starting polyhydroxy compound used. The presence of 3 to 5 equivalents of hydride base per reactive hydroxyl group in the tritylated polyol moiety will generally ensure complete deprotonation of the alcohol to form the alkoxide, without the possibility of reverting back to the alcohols upon protonation. This can occur, provided no excess proton source is purposely introduced into the reaction mixture (i.e., by addition of water or other protic solvents).

After treatment with the hydride base, the reaction mixture is cooled to a temperature of between 0° C. and 25° C., and an alkylating agent is then added thereto. The alkylating agent is generally chosen depending on the R substituent group desired in structure (III) which is the final product. For instance, the alkylating agents that may be used in the present invention include methyl iodide, dimethyl sulfate, methyl bromide, allyl bromide, benzyl bromide, octyl iodide, butyl iodide, halides and sulfonate esters of long chain hydrocarbons, and the like. The concentration of the alkylating agent varies depending upon the amount of starting material present in the reaction medium. It is preferable to use a 5 molar equivalent excess of alkylating agent for each hydroxyl group in the tritylated polyol.

The alkylating agent is added over a period of time at a variety of temperatures which depend upon the alkylating agent used. It is important that the addition of said alkylating agent should be slow and at a temperature to preclude evaporation of the alkylating agent during the reaction.

Two methods may be employed for the removal of primary trityl protecting groups; treatment with acetic acid followed by heating or reductive cleavage by use of a group (I) metal in liquid ammonia and tetrahydrofuran. The latter method is preferable when R is an alkyl group. The former method is preferable if the pendant R groups are allyl or benzyl groups. By treating with acetic acids in the case of disaccharides low yields may result due to acid catalyzed cleavage of the glycosidic linkage.

The preferred method for removal of the primary O-trityl groups when R represents a methyl or alkyl group is by reductive cleavage with an alkali metal. Any alkali metal may be used in this procedure including lithium, sodium, mixtures thereof and the like. Two alkali metals can also be used such as lithium and potassium. It is preferable to use lithium in this procedure, because it is relatively inexpensive, less reactive than other group (I) metals in air, safe to handle in air, and less pyrophoric than any other group (I) metals in the presence of moisture. It is preferable to use a 2 to 5 equivalent excess of the alkali metal for each millimole of triphenylmethyl group present in the molecule. It is even more preferable to use a minimum of 2 equivalent excess alkali metal per mole of the trityl moiety.

The alkali metal is added over a period of time between 30 to 60 minutes and at a temperature between $-65°$ C. to $-78°$ C., more preferably $-70°$ C. The excess alkali metal is then decomposed by the addition of ethanol or isopropanol, and small pieces of solid carbon dioxide may be added to aid in the evaporation of ammonia as the solution is allowed to attain room temperature.

The final product may be further isolated by use of flash column chromatography or any other isolation procedure that will separate the final product from other nonpolar compounds present in the reaction mixture.

In a preferred embodiment, the present invention relates to the synthesis of 2,3,3',4,4'-penta-O-methylsucrose from sucrose by converting sucrose to 1',6,6'-tri-O-trityl-sucrose, which is converted to the tri-O-trityl penta-methyl ether moiety and reduced with an alkali metal in liquid ammonia to form the final product.

The starting compound, sucrose, is first converted to 1',6,6'-tri-O-tritylsucrose by reacting sucrose with trityl chloride. This method is described by Hough et al in the journal, *Carbohydrate Research*, Vol. 21 (1972), pp.414–417, and is incorporated herein with some modifications. Specifically, the process involves the addition of trityl (triphenylmethyl) moieties to the 1', 6, and 6' positions on the sucrose molecule. The synthesis is performed by adding a solution of trityl chloride in dimethylformamide to a solution of sucrose in dimethylformamide and triethylamine. The amount of sucrose used may vary. For instance, between 314 mg (1 mmol) to 70 grams (204.5 mmol) of sucrose may be used. The amount of trityl chloride may also vary depending on the amount of starting sucrose used. For instance, about 4.5 times the molar amount of trityl chloride is used per mole of sucrose, and, therefore, it is preferable to use 260 grams (935 mmol) of tritylchloride per 70 grams (204.5 mmol) of sucrose. After dropwise addition of a solution of trityl chloride in dimethylformamide at 0° to 5° C. over a time period of about one hour, the mixture is allowed to warm to room temperature and then stirred at a constant temperature of about 45° C. for two days. The mixture is then concentrated to about half the original volume under reduced pressure and dissolved in methylene chloride, washed successively with water, 1 M hydrochloric acid, saturated aqueous sodium bicarbonate, water, and brine, and then dried in the presence of sodium sulfate. The methylene chloride is then removed in vacuo. The residue is then applied on a column of silica gel (230 to 400 mesh) and eluted successively with methylene chloride, 10% acetone in methylene chloride and 20% acetone in methylene chloride at a flow rate of about 100 ml/min. 100 ml fractions are collected, and each fraction is spotted on a thin-layer chromatography plate, and the plate is developed with 20% acetone in methylene chloride. Three compounds elute from the column with methylene chloride and 10% acetone in methylene chloride. These three compounds are nonpolar compounds and typically have Rf values of 0.83, 0.74, and 0.62 on silca gel 60 plates (0.25 mm, F-254 E. Merck). The desired 1',6,6'-tri-O-tritylsucrose elutes with 20% acetone in methylene chloride and has an Rf value of 0.21 in 20% acetone in methylene chloride. The yield of 1',6,6'-tri-O-tritylsucrose using this method is typically between 65% and 70%.

The tri-O-tritylsucrose adduct is then O-methylated at positions 2, 3, 3', 4 and 4' to produce 1',6,6'-tri-O-trityl-2,3,3',4,4'-penta-O-methylsucrose. The penta-O-methylation is performed under conditions that take advantage of the fact that a hydride base reacts rapidly with the secondary alcohols to produce hydrogen gas and the said alkoxides, without the possibility of reverting back to the alcohols. The alkoxides are then alkylated with an alkylating agent such as methyl iodide or dimethyl sulfate to produce the penta-O-methyl ethers.

In the synthesis of the intermediate compound, 1',6,6'-tri-O-trityl-2,3,3',4,4'-penta-O-methylsucrose, all group (I) and group (II) metal hydrides, alkyl lithium, and aryl lithium bases, as well as all group (I) and group (II) bases can be used to convert the secondary alcohols to alkoxides. Examples include methyllithium, butyllithium, t-butyllithium, phenyllithium, sodium hydride, potassium hydride, and the like, to mention only a few. It is preferable to use a hydride base such as sodium hydride in the present process.

The amount of group (I) and group (II) metal hydrides and the aforementioned bases utilized in the second step of this process may vary depending on the amount of 1',6,6'-tri-O-tritylsucrose used in the reaction. For scales up to 10 mmol to 10.69 grams of tri-O-tritylsucrose, approximately 6 grams to 10 grams or 150 mmol to 250 mmol of a 60% dispersion of sodium hydride in oil are used. The presence of 3 to 5 equivalents of hydride base per reactive hydroxyl group in tri-O-tritylsucrose will ensure complete deprotonation of the alcohol to form the alkoxide, without the possibility of the alcohol to form the alkoxide, without the possibility of reverting back to the alcohol, provided no excess proton source is purposed introduced into the reaction mixture (i.e., by addition of water or other protic solvents). The excess sodium hydride is added to assure that the reaction mixture stays dry in case traces of moisture are accidentally introduced. If greater than 10 mmol of 1',6,6'-tri-O-tritylsucrose is reacted, i.e., 50 grams (46.76 mmol) to 150 grams (140 mmol), then an equal weight in grams of sodium hydride (60% in oil) is used. Thus, for instance, for 150 grams of tri-O-tritylsucrose, 150 grams (3900 mmol) of sodium hydride (60% dispersion in oil) is used. For large scale synthesis, it is preferable to use 5 equivalent excess of hydride ion for each hydroxyl group in tri-O-tritylsucrose.

The hydride is usually stored as a dispersion in oil at varying concentrations. Prior to using the hydride base in the reaction, it should be washed free of the oil with pentane. Then, the washed hydride is resuspended in a suitable solvent. Any polar aprotic solvent that can suspend or dissolve the hydride may be used, provided the solvent and hydride do not destructively react at the temperatures needed to deprotonate the alcohols. For example, dimethylformamide (DMF) begins to decompose in the presence of sodium hydride at 55° C. to 60° C. within a few hours to produce carbon monoxide and sodium dimethylamide. Examples of suitable hydrides and their corresponding solvent for this reaction include sodium hydride in DMSO, potassium hydride in DMSO at low temperatures of 0° to 40° C., sodium hydride in tetrahydrofuran (THF), potassium hydride in tetrahydrofuran (THF), sodium hydride in HMPA (hexamethylphosphoric triamide), sodium hydride in N-methylpyrrolidone, potassium hydride in N-methylpyrrolidone, sodium hydride in DMSO/THF, potassium hydride in DMSO/THF at low temperatures of 0° to 40° C., sodium or potassium hydrides in DMF at low temperatures of 0° to 40° C., calcium hydride in hexamethylphosphoric triamide, methyllithium, phenyllithium, butyllithium, sec-butyllithium or t-butyllithium in ether solvents such as tetrahydrofuran (THF), dioxane, dimethoxyoxyethane, diethylether or t-butylmethyl ether, alkyl lithium or aryl lithium and magnesium reagents in hexamethylphosphoric triamide or N-methylpyrrolidone, transition metal salts and hydrides of copper, cadmium, cobalt, and the like. It is preferable to use dimethylsulfoxide (DMSO) for a variety of reasons since methyl protons of DMSO are less acidic than the hydroxyl group protons of tri-O-tritylsucrose, DMSO does not completely react with sodium hydride to form the dimsylanion within 30 to 60 minutes at temperatures ranging between 25° C. to 55° C., and the red penta anion of tri-O-tritylsucrose is very soluble in DMSO. Moreover, since only small amounts of the dimsylanion is formed by using DMSO, the anion will react with the hydroxyl groups in tri-O-tritylsucrose to form alkoxides. The amount of solvent used in the present invention may vary depending upon the amount of tri-O-tritylsucrose and hydride used in the reaction. It is preferable to use 10 ml of DMSO per gram of tri-O-tritylsucrose or 0.1 M tri-O-tritylsucrose in DMSO.

The addition of the 1',6,6'-tri-O-tritylsucrose to the hydride base usually takes place at a temperature between 45° C. to 55° C. to permit the formation of alkoxides. It is preferable, however, that the reaction proceed at a temperature of about 50° C. to 60° C., most preferably about 50° C. The internal temperatures do not ever rise above 60° C.

This addition usually takes place over a period of 20 minutes to three hours depending on the amount of starting 1',6,6'-tri-O-tritylsucrose being used. For instance, if up to 10 mmol of the tritylsucrose is being reacted, then the addition takes place over a period of about 30 minutes. If the starting tritylsucrose concentration is greater than 10 mmol, then the addition to the hydride base may take up to 3 hours. The 1',6,6'-tri-O-tritylsucrose is added dropwise 3 hours. The 1',6,6'-tri-O-tritylsucrose is added dropwise under constant stirring while the reaction temperature is monitored by placing a thermometer in the reaction vessel. After the addition of the tritylsucrose, the reaction mixture is maintained at the above-described temperature and constantly stirred for an additional time period. Usually this period is approximately 90 minutes.

After hydrogen evolution has ceased completely, a burgundy-red solution is obtained. This solution is then cooled to a temperature between 0° C. and 25° C.

Upon cooling the reaction mixture, an alkylating agent is then added dropwise over a varying time period, depending on the amounts of alkylating agents being added. For instance, in preparation containing up to 10 mmol of the tritylsucrose, the alkylating agent may be added over a period of about 30 minutes since less of the alkylating agent is used in the reaction. For preparations of larger than 10 mmol, the alkylating agent may be added over a time span of up to 90 minutes.

Any alkylating agent may be used in the present invention that will add an alkyl moiety to the alkoxide. Examples of the alkylating agents, which may be used in the present invention include methyl iodide, dimethyl sulfate, methyl chloride, methyl bromide, allyl bromide, benzyl bromide, octyl iodide, butyl iodide, halides and sulfonate esters of long chain hydrocarbons, and the like. If methyl iodide is used in this method, then it is usually freshly distilled over copper. The concentration of the alkylating agent may vary depending upon the amount of starting material present in the reaction medium. It is preferable to use a 5 molar equivalent excess of alkylating agent for each hydroxyl group in tri-O-tritylsucrose. Thus, for example, if 100 mmol of tri-O-tritylsucrose is used, 500 mmol of hydroxyl groups/100 mmol tri-O-tritylsucrose react and therefore 2,500 mmol of alkylating agent is used.

The alkylating agent is added over a period of time at a variety of temperatures, which depend upon the alkylating agent used. For instance, if methyl iodide is used, the reaction should be cooled to 0° C. and should not rise above 10° C. during the reaction. The addition of said alkylating agent should be very slow to preclude the internal temperature of the reaction from rising to the boiling point since the alkylating agent may evaporate. The reaction is then stirred at room temperature for a period between 2 to 24 hours. At this point, the mixture can be concentrated to one-fifth the volume at a temperature of about 60° C. under 0.1 mm Hg, if desired. Then the solution or concentrated solution is treated with a 10% solution of sodium hydroxide and stirred for an additional time period. After the addition of the sodium hydroxide, the resulting mixture is then diluted with water and an extracting agent such as methylene chloride or ethyl acetate. The extraction with the solvents is usually repeated at least twice, and the organic extracts are combined and further washed with water and brine. The washed organic extracts are then further dried over anhydrous magnesium sulfate, filtered, and concentrated in vacuo to provide a residue.

The residue is then placed over a silica gel column and the final product is eluted therefrom with a 1:1 hexane:methylene chloride solution of approximately liters; followed by methylene chloride and 5% ethyl acetate in methylene chloride. The flow rate of the column varied between 100 ml/min to 200 ml/min.

The yield of 1',6,6'-tri-O-trityl-2,3,3',4,4'-penta-O-methylsucrose obtained by the above process is between 89% to 97%.

The 1',6,6'-tri-O-trityl-2,3,3',4,4'-penta-O-methylsucrose obtained is converted to 2,3,3',4,4'-penta-O-methylsucrose by unmasking the tri-O-trityl protecting groups to regenerate the hydroxyl groups at positions 1', 6 and 6'. The trityl groups are removed by reduction without adversely effecting the glycosidic linkage. This reductive cleavage is performed by using alkali metals in the presence of liquid ammonia in a suitable aprotic solvent such as tetrahydrofuran (THF). Alternatively, the triphenylmethyl protecting groups may be removed by treatment of the tritritylpentamethyl adduct of sucrose with acetic acid. Here the yields may be low possibly due to cleavage of the sucrose to produce O-methylated glucose and fructose derivatives.

Any alkali metal can be used in the present procedure such as lithium, sodium and the like. Two alkali metals may also be used such as lithium and sodium. It is preferable, however, to use lithium in this reduction procedure, because it is relatively inexpensive, is less reactive than other group (I) metals in air, is safe to handle in air and is less pyrophoric than any other group (I) metals in the presence of moisture.

The tritylated penta-O-methylsucrose is diluted in tetrahydrofuran (THF) and liquid ammonia. It is preferable to use approximately 1 liter of tetrahydrofuran for every 100 grams of tri-O-trityl-penta-O-methylsucrose; however variations from this amount do not affect the yield of the final product. For example, 45 to 50 grams of tri-O-trityl-2,3,3',4,4'-penta-O-methylsucrose can be dissolved in 1.0 liter of tetrahydrofuran (THF), or 288 grams of tri-O-trityl-2,3,3',4,4'-penta-methylsucrose can be dissolved in 2.5 liters of THF. If 288 grams (253 mmol) of 1',6,6'-tri-O-trityl-2,3,3',4,4'-penta-O-methylsucrose is dissolved in 2.5 liters of dry tetrahydrofuran, then the mixture is cooled to $-70°$ C. Into this solution is distilled approximately 2.5 liters of liquid ammonia, and the mixture is treated with small pieces of lithium (12 grams, 1,714 mmol, 6.7 equivalent). It is preferable to use 2 to 5 equivalent excess of lithium for each millimole of triphenylmethyl group present in the molecule. It is more preferable to use a minimum of 2 equivalent excess alkali metal per mole of the trityl moiety. The addition of the alkali metal generally takes place over a time period of 30 to 60 minutes depending upon the quantities involved. In this instance, the addition time is about 60 minutes. The color of the reaction mixture after addition of the alkali metal is deep red. The reaction mixture is allowed to stir for about three hours at a temperature between $-65°$ C. to $-78°$ C., more preferably at $-70°$ C. The excess alkali metal is then decomposed by the addition of ethanol or isopropanol. However, it is preferable to use ethanol, since it can be easily removed in vacuo. Approximately 0.1 ml of ethanol is added per millimole of alkali metal used. Small pieces of solid carbon dioxide are also added after destroying the lithium metal to aid in the evaporation of ammonia as the solution is allowed to attain room temperature.

The resulting mixture is then filtered, the inorganic retentate is washed thoroughly with acetone, and the effluent is concentrated to a thick yellow oil. Flash column chromatography of the concentrated oil on a column of silica gel using 50% ethyl acetate in methylene chloride separates the triphenylmethane and other nonpolar components of the reaction mixture. 2,3,3',4,4'-Penta-O-methylsucrose is then eluted from the column with 10% ethanol in methylene chloride. The yield of the 2,3,3',4,4'-penta-O-methylsucrose from this isolation procedure is 95% to 97%.

Figure 8:
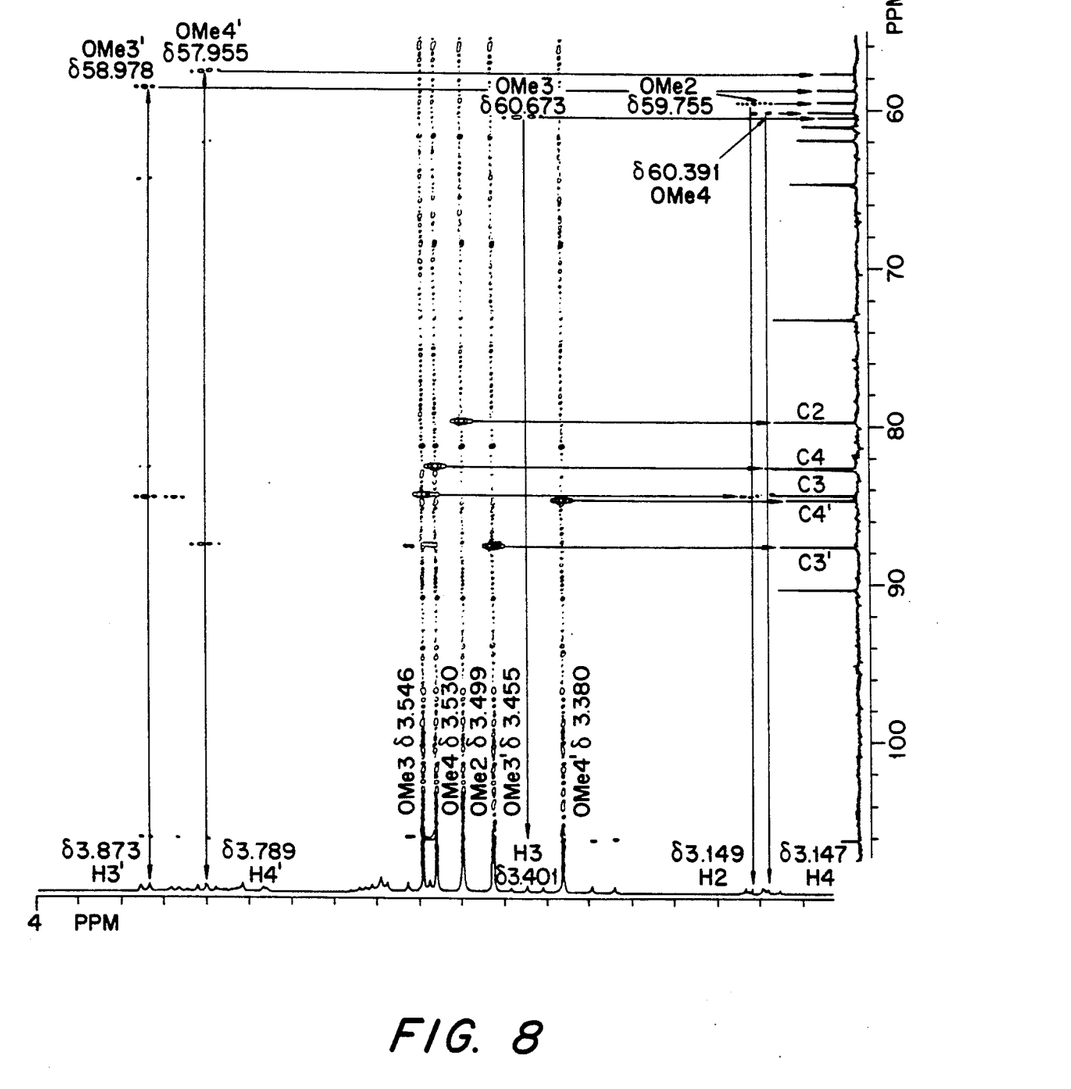
FIG. 8 is a heteronuclear multiple bond connectivity (HMBC) spectrum of 2,3,3',4,4'-penta-O-methylsucrose synthesized by the process of the present invention.

FIG. 8 illustrates a heteronuclear multiple bond conductivity spectrum (HMBC) performed on 2,3,3',4,4'-penta-O-methylsucrose synthesized from the above-described procedure. HMBC is an NMR technique used to correlate resonances or signals of carbon and hydrogen atoms within a molecule which molecule is separated by a heteroatom such as oxygen or nitrogen. Specifically, 512-2K blocks of 64 scans were recorded using a delay of 80 ms for the evolution of the long-range coupling and a 3.6 ms delay for the removal of the direct correlation. The final data set was multiplied by a sine-bell function in both domains and zero filled to yield a 1K×1K real data matrix. The sample temperature was regulated at 25° C. and the sample was not spun.

This spectrum illustrates the connectivity of the O-methyl moieties to the methine protons on sucrose and confirms that the aforedescribed compound produced by the process of the present invention is 2,3,3',4,4'-penta-O-methylsucrose.

2,3,3',4,4'-Penta-O-methylsucrose synthesized by the process of the present invention is a versatile intermediate that can be used in a variety of different applications. First of all, penta-O-methylsucrose can be used neat as a cross linking agent for preparing cross-linked polyesters. Moreover, the manipulation of the three primary hydroxyl groups can result in variety of trifunctional monomers that can be used as cross linking agents for poly vinyl ethers, vinyl and allyl polymers, nylons, polyacrylamides and the like. These monomers may be found in the development of various cross-linked polymers, network polymers or starburst polymers. In addition, some of the trifunctional monomers produced in this way such as triamine and tricarboxylic acid derivatives of penta-O-methylsucrose make excellent tridentate ligands for metal complexation.

Polyhydroxy compounds containing 2-primary hydroxyl groups, i.e., addition to other secondary alcohols after tritylation, alkylation and the deprotection series will provide diols. These diols may be used for the preparation of linear polyethers and polyesters. In addition, the diols may be modified to generate other polyesters, polyethers, polyamides, polyamines, and polyurethanes. The diols and diamines may be converted to the corresponding diacrylates, diacrylamides, dimethacrylates, and dimetharylamides for the development of linear and cross-linked acrylate, methacrylate, and acrylamide addition polymers. Divinyl ethers of these diols may be used for preparing linear and cross-linked vinyl ether polymers.

Asymmetric reducing agents are also contemplated from the present invention. Because naturally occurring materials such as sucrose and derivatives thereof are asymmetric, they can be used in conjunction with other organic or inorganic materials to produce coordination or organometallic complexes which show proclivity to attack one face or the other of a double bond with high selectivity. This selective mode of attack is known as asymmetric synthesis and the agent effecting the transformation is called an asymmetric reagent. Thus, the presently disclosed penta-O-methylsucrose compound can be further used to synthesize asymmetric reagents that can be used in conjunction with certain metals to facilitate the synthesis of artificial enzyme mimics or industrially useful asymmetric reagents and catalysts for reductions and carbon-carbon bond formations.

In order to further illustrate the present invention and the advantages thereof, the following specific examples are given, it being understood that same are intended only as illustrative and in nowise limitative.

EXAMPLE 1

A. Synthesis of 1',6,6'-tri-O-tritylsucrose

The procedure of Hough, Mufti, and Khan, *Carbohydrate Res.*, Vol. 21, pp. 144–147 (1972), is modified as shown below. To a solution of 15 g of sucrose (43.82 mmol) in 225 ml of pyridine, a solution of 54.95 g of trityl chloride (197.1 mmol, 4.5 equiv.) in 50 ml of pyridine is added dropwise over a period of 30 minutes. The reaction mixture is then stirred at room temperature for 4 days. After 4 days, the solution is concentrated to a brown syrup, which is dissolved in methylene chloride. This solution is further washed successively with 1 M hydrochloric acid, saturated sodium bicarbonate solution, water, and brine and then dried over anhydrous sodium sulfate. The methylene chloride solution is then concentrated in vacuo and the residue applied on a column of silica gel packed in methylene chloride:acetone (4:1) and eluted with that solvent. The 1',6,6'-tri-O-tritylsucrose is obtained (28.59 g) in 58.8% yield as an off-white solid with a melting point of 127° to 130° C.

B. Synthesis of 1',6,6'-tri-O-tritylsucrose

On scales larger than 40 mmol, the following procedure can be used. However, the yields established in the method shown are reproducible on scales ranging from 1 mmol to 210 mmol.

In a dry 5-L four-neck flask is dissolved 70 grams of sucrose (204.5 mmol) in 1 liter dry dimethylformamide (DMF) and dry triethylamine (200 ml, 145 grams, 1,423 mmol). The solution is allowed to attain a temperature of 25° to 30° C. and treated with a solution of trityl chloride (260 grams, 935.2 mmol, 4.5 equiv.) in dimethylformamide (600 ml), added dropwise over 1 hour. After the addition is complete, the reaction mixture is heated to a temperature of 50° C. and allowed to stir for 48 hours at that temperature. After 2 days, the reaction mixture is filtered through a short pad of silica gel to remove the precipitated triethylammonium hydrochloride and the residue is washed with methylene chloride:acetone (4:1). The effluent is then concentrated to a residue, which is reconstituted in methylene chloride and washed successively with 1 N hydrochloric acid, saturated sodium bicarbonate solution, water, and brine and then dried over anhydrous sodium sulfate. The dry organic extract is then filtered and concentrated in vacuo to provide a yellow foamy solid. This material is then applied on a silica gel column (230 to 400 mesh, 10 cm x 50 cm) packed with methylene chloride and successively eluted with methylene chloride, then 10% acetone in methylene chloride, followed by elution with 20% acetone in methylene chloride. The desired tri-O-tritylsucrose elutes with 20% acetone in methylene chloride and has an $R_f$ of 0.21 in the same solvent. The amount of 1',6,6'-tri-O-tritylsucrose obtained by this method of synthesis and isolation is typically between 146 to 150 grams or 67% to 68.8%. On scales between 1 mmol and 50 mmol(314 mg to 15.7 grams) yields average about 76%.

Figure 1:
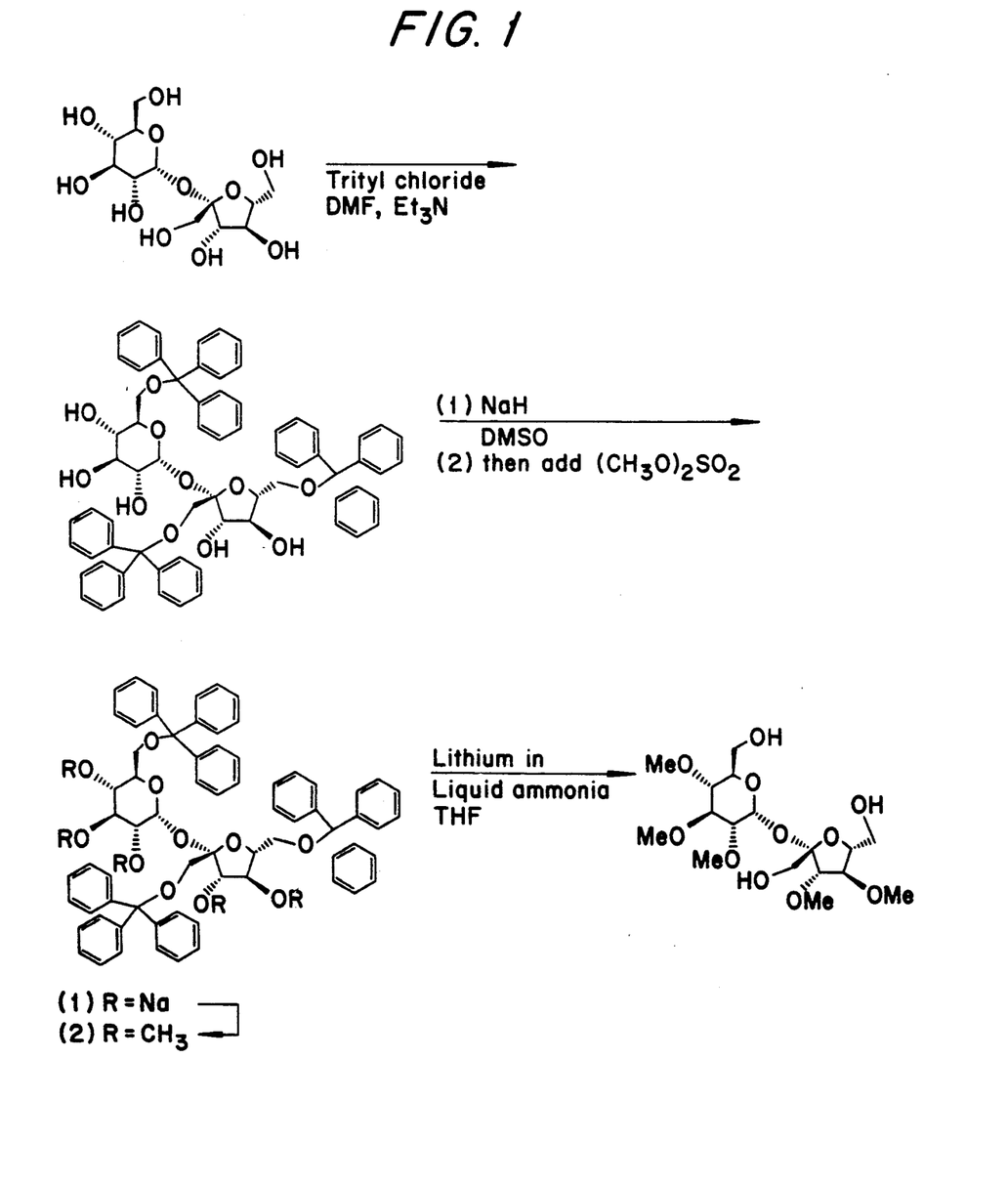
FIG. 1 represents the synthesis of 2,3,3',4,4'-penta-O-methylsucrose according to the process of the present invention.
Figure 2:
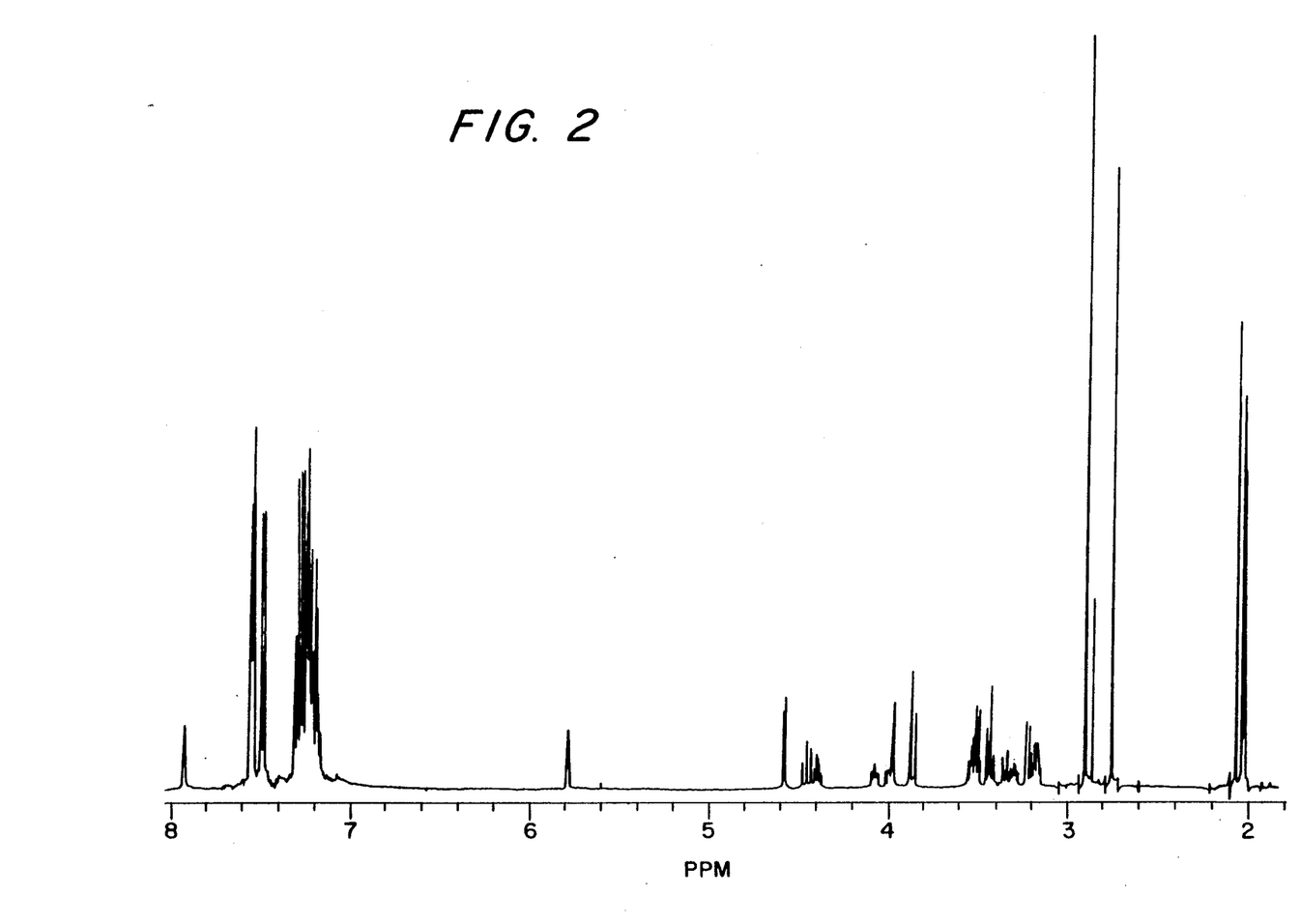
FIG. 2 is an $^1$H NMR spectrum of 1',6,6'-tri-O-tritylsucrose synthesized by the process of the present invention.
Figure 3:
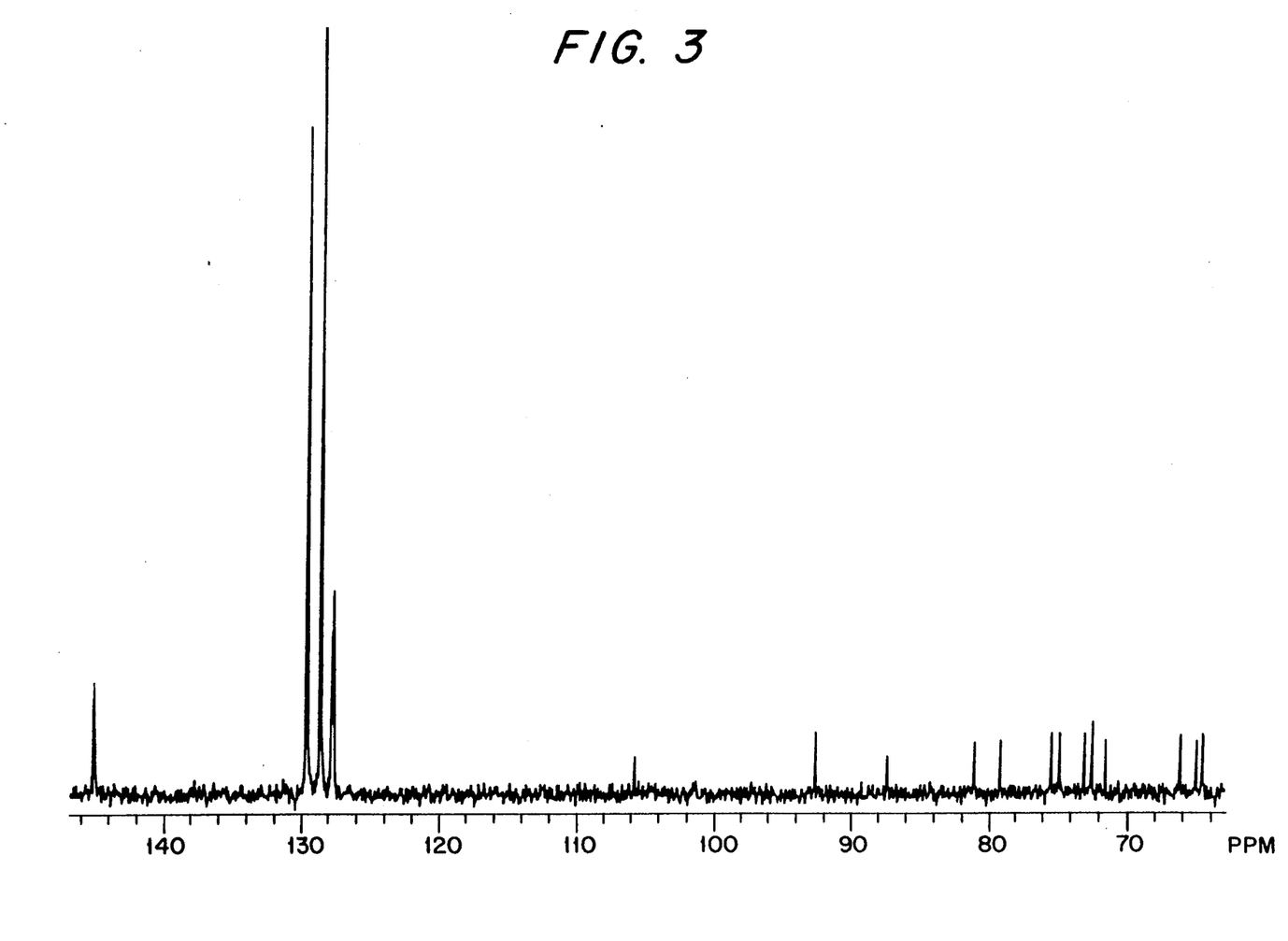
FIG. 3 is a $^{13}$C NMR spectrum of 1',6,6'-tri-O-tritylsucrose synthesized by the process of the present invention.

FIGS. 2 and 3 illustrate the respective NMR spectra of 1',6,6'-tri-O-tritylsucrose.

C. Synthesis of 1',6,6'-tri-O-trityl-2,3,3',4,4'-penta'-O-methylsucrose

Figure 4:
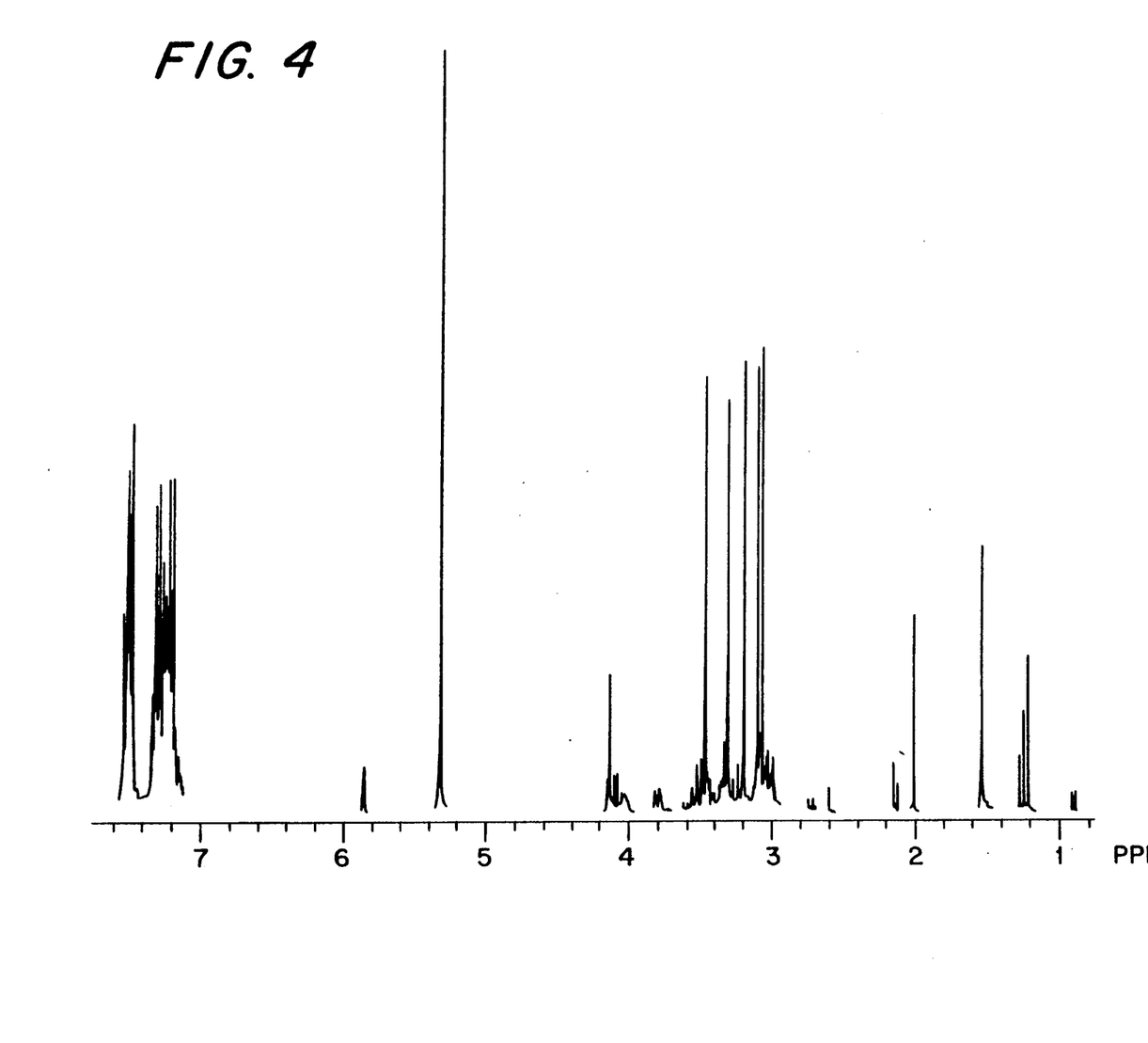
FIG. 4 is an $^1$H NMR spectrum of 1',6,6'-tri-O-trityl-2,3,3',4,4'-penta-O-methylsucrose synthesized by the process of the present invention.
Figure 5:
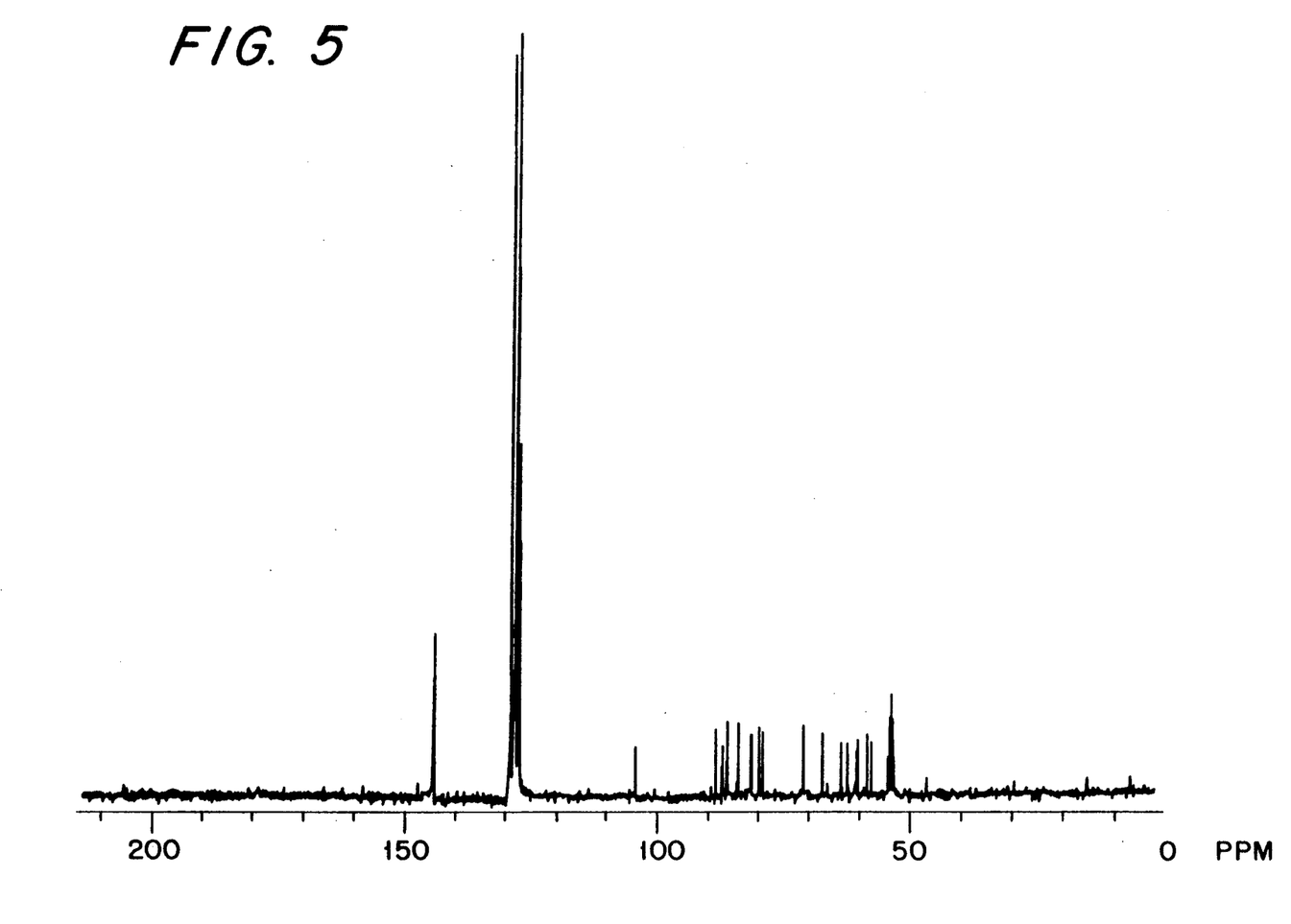
FIG. 5 is a $^{13}$C NMR spectrum of 1',6,6'-tri-O-trityl-2,3,3',4,4'-penta-O-methylsucrose synthesized by the process of the present invention.

On scales larger than 10 mmol the following procedure is used. To a dry 5-L four-neck flask is added sodium hydride (60% in oil, 150 grams, 1250 mmol), washed free of oil with pentane and suspended in DMSO (800 ml). The suspension is heated to 50° C., mechanically stirred, and treated with a solution of 1,6,6'-tri-O-tritylsucrose (50 grams, 46.76 mmol, dissolved in DMSO 200 ml, and added dropwise over 2 hours). The temperature of the reaction is monitored internally and maintained between 50° C. and 55° C. during the course of addition and 90 minutes thereafter. After hydrogen evolution has ceased completely, the burgundy-red solution is cooled to 25° C. and treated with dimethyl sulfate (147.5 grams, 1175 mmol, 111 ml, added dropwise over 90 minutes). The reaction is stirred at room temperature for 24 hours, treated with aqueous sodium hydroxide (10% solution, 500 ml), and stirred for an additional 3 hours. The mixture is then diluted with water (500 ml) and methylene chloride (500 ml) and the phases separated. The aqueous layer is re-extracted with methylene chloride (4×300 ml), then the organic extracts are combined, washed with water and brine, dried over anhydrous magnesium sulfate, filtered, and concentrated in vacuo. The glassy residue is flash-chromatographed over a column of silica gel (10 cm×15 cm) and eluted with hexanes:methylene chloride (1:1, 2 L), then methylene chloride (2 L) followed by 5% ethyl acetate in methylene chloride (2 L), at a flow rate of about 200 ml/min. The isolated product (mp 103°–108° C.) weighed 47.1 grams (41.35 mmol) and a 89% yield is obtained. $R_f$ of the tritylated methylsucrose is 0.15 in methylene chloride and $[\alpha]_D^{27}=47.68$. in methylene chloride. FIGS. 4 and 5 illustrate the respective NMR spectra for this product. The NMR data provided: $^1$H NMR (500.11 MHz, acetone-D$_6$) δ3.04 (H-2, dd, J=3.5, 9.5 Hz), 3.06 (H-1'a, d, J=10 Hz), 3.07 (H-6a, dd, J=3, 10 Hz), 3.14 (OMe-3', s), 3.16 (OMe-4', s), 3.19 (OMe-2, s), 3.21 (H-3, t, J=9.5 Hz), 3.31 (OMe-4, s), 3.36 (H-1'b, d, J=10 Hz), 3.41 (OMe-3, s), 3.41 (H-6b, J=2, 10 Hz), 3.51 (H-6'a, m), 3.53 (H-4, dd, J=9.5, 10 Hz), 3.55 (H-6'b, m), 3.88 (H-5, ddd, J=2, 3, 10 Hz), 4.17 (H-3, d, J=8.5 Hz), 4.29 (H-4', t, J=8.5 H), 4.41 (H-5', m), 5.98 (H-1, d, J=3.5 Hz), 7.34 (30H arom), 7.52 (15H arom). $^{13}$C NMR (125.76 MHz, acetone-D$_6$) δ57.73 (OMe-3'), 58.36 (OMe-4'), 58.68 (OMe-2), 60.46 (OMe-4), 60.60 (OMe-3), 62.97 (CH$_2$-6'), 63.89 (CH$_2$-6), 67.86 (CH$_2$-1'), 71.41 (CH-5), 79.52 (CH-5'), 80.17 (CH-4), 81.50 (CH-4'), 82.35 (CH-2), 84.52 (CH-3), 86.74 (1'-C-trityl methine), 86.93 (CH-3'), 87.51 (6-C-trityl methine), 87.68 (6'-C-trityl methine), 88.92 (CH-1), 104.66 (CH-2'), 127.22 (CH), 127.43 (2CH), 128.07 (2CH), 128.23 (3CH), 128.27 (CH), 129.03 (2CH), 129.14 (4CH), 144.05(C); 144.32 (2C); FAB mass for C$_{74}$H$_{74}$O$_{11}$ calculated 1138.33; found M$^+$+1 =1139, M$^+$−H+K$^+$=1177, M$^+$+K$^+$=1178. Anal.

Calc. for C₇₄H₇₄O₁₁:C,78.0; H,6.5; 0,15.5. found: C, 77.5; H, 6.5.

After scale-up of this reaction employing 150 g tri-O-tritylsucrose (140 mmol), 150 g of sodium hydride (60% in oil, 3,900 mmol); 1,600 ml of dimethylsulfoxide; and 330 ml of dimethyl sulfate (441 g, 3,500 mmol) was performed under exactly the same conditions discussed above. After chromatography on a column of silica gel (230 to 400 mesh, 10 cm × 50 cm) and elution with three times the quantities of solvents discussed above, 145.15 g of tri-O-trityl-penta-0methylsucrose was obtained in 91% yield.

D. Synthesis of 2,3,3',4,4'-penta-O-methylsucrose

To a 40 mmol solution of 1',6,6'-tri-O-trityl-2,3,3',4,4'-penta-O-methylsucrose (45.6 grams) in 1 liter of dry tetrahydrofuran and 2 liters of liquid ammonia at −70° C. is added 4 grams of small pieces of lithium wire. The lithium wire is added over a period of over 50 minutes and a deep-red solution is obtained. This solution is further stirred for 3 hours at −70° C. The excess lithium is decomposed by adding 60 ml of ethanol. Small pieces of solid carbon dioxide are also added to evaporate the ammonia as the solution approaches room temperature. The resulting mixture is then filtered, and the inorganic retentate is washed thoroughly five times with 300 mls of acetone. The effluent is then concentrated to a thick yellow oil.

The product is then purified by flash column chromatography according to the guidelines of Still, Kahn and Mitra, *J. Org. Chem.*, Vol. 43 (1978), pp. 2923-2925, on 230-400 mesh silica gel.

The oil is then placed on a silica gel column (10 cm × 15 cm) and is washed with a solution containing 50% ethyl acetate in methylene chloride at a flow rate of 200 ml/min. This wash separates out the triphenylmethane and other nonpolar components of the reaction mixture.

Figure 6:
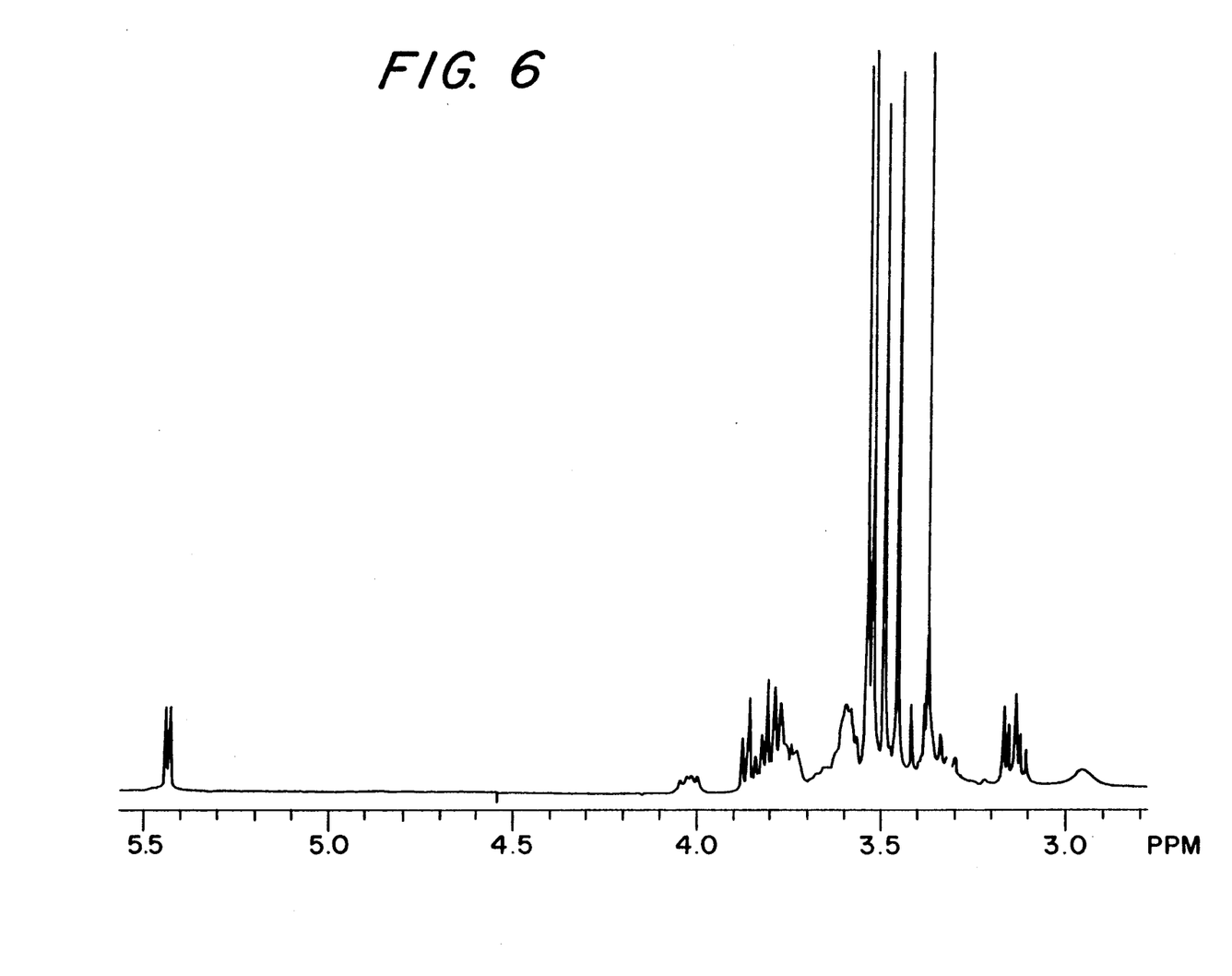
FIG. 6 is an $^1$H NMR spectrum of 2,3,3',4,4'-penta-O-methylsucrose synthesized by the process of the present invention.
Figure 7:
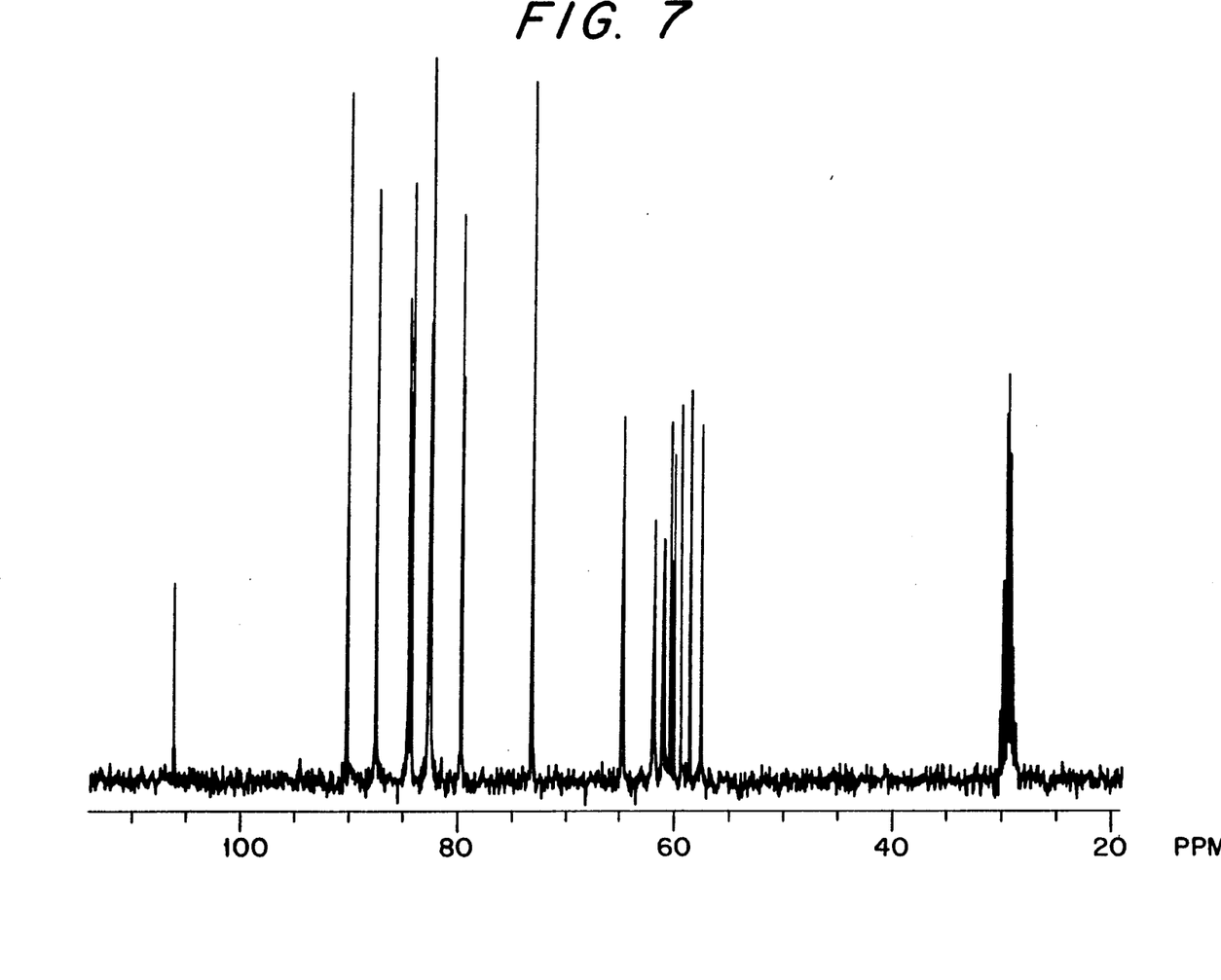
FIG. 7 is a $^{13}$C NMR spectrum of 2,3,3',4,4'-penta-O-methylsucrose synthesized by the process of the present invention.

2,3,3',4,4'-Penta-O-methylsucrose is eluted from the column with a 10% ethanol in methylene chloride solution. 16.11 Grams, 39.10 mmol of 2,3,3',4,4'-penta-O-methylsucrose is obtained, and the yield of this product is 97%. $R_f$ in 5% ethanol in methylene chloride is 0.31 and $[\alpha]_D^{27} = 50.60°$ in acetone. ¹H NMR (500.11 MHz, acetone D₆) δ3.15 (H-4, t, $J_{3',4'}=5.1$ Hz, $J_{4,5}=9.0$ Hz), 3.15 (H-2, dd, $J_{1,2}=3.7$ Hz, $J_{2,3}=9.8$ Hz), 3.33 (H-1'a, d, $J_{1'a,1'b}=-12.5$ Hz), 3 38 (OMe-4', s), 3.40 (H-3, t, $J_{3,4}=9.8$ Hz), 3.46 (OMe-3', s), 3.50 (OMe-2, s), 3.53 (OMe-4, s), 3.55 (OMe-3, s), 3.55 (H-1'b,d), 3.59 (H-6'a, m, $J_{6'a,6'b}=12.0$ Hz), 3.60 (H-6a, dd, $J_{5,6a}=5$ Hz, $J_{6a,6b}=-10.6$ Hz), 3.61 (H-6'b, m, $J_{6'a,6'b}=-12.0$ Hz), 3.75 (H-6b, dd, $J_{5,6b}=2.1$ Hz, $J_{6a,6b}=10.6$ Hz), 3.78 (H-5, m, $J_{5,6a}=5$ Hz, $J_{5,6b}=2.1$ Hz), 3.80 (H-4', t, $J_{3',4'}=5.1$ Hz, $J_{4',5'}=5.8$ Hz), 3.84 (H-5', m, $J_{5',6'a}=4.2$ Hz, $J_{5'6'b}=6.3$ Hz), 3.87 (H-3', d, $J_{3',4'}=5.1$ Hz), 5.45 (H-1, d, $J_{1,2}=3.7$ Hz). ¹³C NMR (125.76 MHz, acetone D₆) δ57.96 (OMe-4'), 58.98 (OMe-3'), 59.76 (OMe-2), 60.29 (CH₂-6), 60.39 (OMe-4), 60.67 (OMe-3), 61.79 (CH₂-6'), 64.63 (CH₂-1'), 73.12 (CH-5), 79.53 (CH-2), 82.48 (CH-4), 82.59 (CH-5'), 84.24 (CH-3) 84.52 (CH-4'), 87.48 (CH-3'), 90.17 (CH-1), 106.80 (C-2'). FDMS for C₁₇H₃₂O₁₁ calculated 412.43; found M+1=413. FIGS. 6 and 7 illustrate the respective NMR spectra of 2,3,3',4,4'-penta-O-methylsucrose. Anal. Calc for C₁₇H₃₄O₁₁ C, 49.5; H, 7.5; 0, 42.8 Found: C, 49.2; H, 7.8.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

I claim:

1. A process for the synthesis of 2,3,3',4,4'-penta-O-methylsucrose comprising the steps of:
   (a) converting sucrose to 1',6,6'-tri-O-tritylsucrose with trityl chloride;
   (b) treating the converted 1',6,6'-tri-O-tritylsucrose with a hydride base to produce a pentaoxy anion sucrose intermediate;
   (c) alkylating said pentaoxy anion with an alkylating agent at a temperature to preclude evaporation of said alkylating agent to form 1',6,6'-tri-O-trityl-2,3,3',4,4'-penta-O-methylsucrose;
   (d) reducing trityl groups with an alkali metal in the presence of ammonia to convert the 1',6,6'-tri-O-trityl-2,3,3',4,4'-penta-O-methylsucrose to 2,3,3',4,4'-penta-O-methylsucrose; and
   (e) isolating 2,3,3',4,4'-penta-O-methylsucrose.

2. The process according to claim 1, wherein said sucrose is converted using a solution of trityl chloride in pyridine and dimethylformamide.

3. The process according to claim 2, wherein 30 to 90 grams of trityl chloride in 35 to 110 ml of pyridine is added to 10 to 30 grams of sucrose diluted in 150 to 450 mls of pyridine.

4. The process according to claim 3, wherein said trityl chloride in pyridine is added dropwise during a period of 30 minutes to said sucrose solution.

5. The process according to claim 1, wherein said 1,',6,6'-tri-O-tritylsucrose is further isolated by thinlayer chromatography.

6. The process according to claim 1, wherein said hydride base is selected from the group consisting of group (I) metal hydrides, group (II) metal hydrides, alkyllithium, aryllithium, group (I) bases, group (II) bases, and admixtures thereof.

7. The process according to claim 6, wherein said hydride base is sodium hydride.

8. The process according to claim 7, wherein said sodium hydride is diluted in dimethylsulfoxide.

9. The process according to claim 1, wherein (b) is performed at a temperature between 50° C. to 60° C.

10. The process according to claim 1, wherein said alkylating agent is methyl iodide, dimethyl sulfate, methyl chloride or methyl bromide.

11. The process according to claim 10, wherein said alkylating agent is dimethyl sulfate.

12. The process according to claim 1, wherein (c) is performed at a temperature of 25° C.

13. The process according to claim 1, further comprising the step of isolating 1',6,6'-tri-O-trityl-2,3,3',4,4'-penta-O-methylsucrose after alkylation.

14. The process according to claim 13, wherein said isolating step further comprises the steps of:
   (a) extracting the 1',6,6'-tri-O-trityl-2,3,3',4,4'-penta-O-methylsucrose, with an organic extractant;
   (b) chromatographing the organic extractant; and
   (c) eluting 1',6,6'-tri-O-trityl-2,3,3',4,4'-penta-O-methylsucrose from the chromatograph.

15. The process according to claim 1, wherein said alkali metal is selected from the group consisting of sodium, potassium, and admixtures thereof.

16. The process according to claim 15, wherein said alkali metal is lithium.

17. The process according to claim 1, wherein (d) is performed at a temperature of between −50° C. to −80° C.

18. The process according to claim 1, wherein 1 gram of lithium is added per 11.4 grams of 1',6,6'-tri-O-trityl-2,3,3',4,4'-penta-O-methylsucrose.

19. The process according to claim 1, wherein said alkali metal is adding over a period of over 50 minutes.

20. The process according to claim 1, wherein said 2,3,3',4,4'-penta-O-methylsucrose is isolated by flash column chromatography.

* * * * *